United States Patent [19]
Taylor et al.

[11] Patent Number: 5,308,621
[45] Date of Patent: May 3, 1994

[54] ASCORBIC ACID COMPOSITION AND TRANSDERMAL ADMINISTRATION METHOD

[75] Inventors: Reginald M. Taylor, Hawthorn; David J. Wilson, Balmain, both of Australia

[73] Assignee: Commonwealth Scientific and Industrial Research Organisation, Campbell, Australia

[21] Appl. No.: 795,499

[22] Filed: Nov. 21, 1991

[30] Foreign Application Priority Data

Feb. 18, 1991 [AU] Australia ............................. PK4651
Aug. 19, 1991 [AU] Australia ............................. PK7846

[51] Int. Cl.$^5$ .................. A61K 6/00; A01N 43/08
[52] U.S. Cl. ................... 424/401; 514/474; 514/845; 514/859; 514/863; 514/951
[58] Field of Search .............. 424/448, 401; 514/474, 514/947

[56] References Cited

U.S. PATENT DOCUMENTS

| | | | |
|---|---|---|---|
| 3,215,602 | 11/1965 | Diamond | 514/474 |
| 4,229,430 | 10/1980 | Fahim et al. | 424/49 |
| 4,294,852 | 10/1981 | Wildnauer | 514/474 |
| 4,424,232 | 1/1984 | Parkinson | 514/474 |
| 4,555,524 | 11/1985 | Gruber et al. | 514/570 |
| 4,665,063 | 5/1987 | Bar-Shalom | 514/164 |
| 4,800,086 | 1/1989 | Buehler | 424/497 |
| 4,818,521 | 4/1989 | Tamabuchi | 424/62 |
| 4,832,953 | 5/1989 | Campbell et al. | 424/448 |
| 4,834,978 | 5/1989 | Nuwayser | 424/448 |
| 4,849,418 | 7/1989 | Lohner et al. | 514/163 |
| 4,859,696 | 8/1989 | Kamiya | 514/946 |
| 4,880,633 | 11/1989 | Loper et al. | 424/449 |
| 4,919,921 | 4/1990 | Hatae | 424/62 |
| 4,927,687 | 5/1990 | Nuwayser | 424/449 |
| 4,983,382 | 1/1991 | Wilmott et al. | 424/62 |
| 5,045,317 | 9/1991 | Chess | 424/401 |

FOREIGN PATENT DOCUMENTS

| | | |
|---|---|---|
| 27427/88 | 6/1989 | Australia . |
| 751951 | 9/1933 | France . |
| 948326 | 7/1949 | France . |
| 90/12572 | 11/1990 | PCT Int'l Appl. . |
| 2022998 | 12/1979 | United Kingdom . |

OTHER PUBLICATIONS

Bulletin Officiel De La Propriete Industrielle 2,209,544, Published Dec. 7, 1973 (Syntex, U.S.A. Inc.) p. 11868.
Journal of Pharmaceutical Sciences, vol. 75, No. 3, Mar. 1986; Effect of Particle Dissolution Rate on Ocular Drug Bioavailability; Hui et al.
Patel U. and Banskar U., Il Pharmaco, vol. 45, No. 5, pp. 559-568, (Exhibit A).

Primary Examiner—Gabrielle Phelan
Attorney, Agent, or Firm—Merchant, Gould, Smith, Edell, Welter & Schmidt

[57] ABSTRACT

The present invention concerns a composition for topical application to deliver ascorbic acid by transdermal migration. The composition includes fine particulate ascorbic acids suspended in a pharmaceutically acceptable carrier. The invention also concerns methods of treatment, involving such a composition.

7 Claims, 1 Drawing Sheet

ASCORBIC ACID COMPOSITION AND TRANSDERMAL ADMINISTRATION METHOD

The present invention relates to a composition incorporating ascorbic acid and to methods of transdermal administration of ascorbic acid using such compositions.

The intake of ascorbic acid is required for maintenance of health in animals. Ascorbic acid is essential to maintain the attractive skin appearance in humans and is believed to be effective in reducing the deleterious effects of the sun and ageing on the human skin. Consequently considerable research has been conducted into compositions and methods for providing transdermal delivery of ascorbic acid.

The inherent properties of ascorbic acid make the task of providing compositions for transdermal delivery extremely difficult. Ascorbic acid is notoriously unstable and although it is soluble in water its propensity to oxidise in aqueous solution and/or degrade due to attack by water itself make it desirable to minimise the use of water. On the other hand, the solubility of ascorbic acid in non-aqueous solvents is relatively poor. Consequently despite numerous attempts to produce stable compositions for transdermal delivery concentrations of ascorbic acid in commercially useful formulations have generally been limited to less than 0.1%.

U.S. Pat. No. 4,983,382 and International Patent Application PCT/US90/01968 describe compositions comprising higher concentration of ascorbic acid using water and a co-solvent such as an alcohol or glycol. However these inventions rely on presence of water to solubilise sufficient ascorbic acid to provide an effective composition.

Surprisingly we have found that an effective composition of ascorbic acid is provided using a pharmaceutically acceptable carrier without the need to dissolve the available ascorbic acid if the ascorbic acid is present in the form of fine particles.

We therefore provide a composition comprising ascorbic acid and a pharmaceutically acceptable carrier wherein at least part of the ascorbic acid is present in the form of fine particles dispersed through the composition wherein said fine particles are of a size sufficiently small to provide an effective rate of transdermal transfer of the ascorbic acid from the particles.

Despite the fact that ascorbic acid particles present in the compositions of the invention are of a size previously considered too large to pass through the epidermis, ascorbic acid present in this form has been found to provide an effective rate of transdermal transfer. It is preferred that the particles of ascorbic acid are predominantly sized below 20 microns. More preferably they are predominantly in the range of from 2–10 microns.

In a preferred composition of the invention a small portion of the ascorbic acid is present in the form of a saturated or supersaturated solution in the carrier. Typically the portion of ascorbic acid in solution will be less than 0.1% by weight of the composition and preferably the weight ratio of soluble ascorbic acid to fine particulate ascorbic acid will be less than 0.1:1.

The particle size of the crystals may be determined by microscopic examination. It should be assumed that the crystals are of a constant thickness. The surface area of each visible crystal face should be determined, and the particle size calculated by calculating the square root of the measured surface area. This value should then be taken to be the average length of side. The total area of the counted particles should be measured and the sum of the areas of the different size ranges estimated as a percentage of the total.

The particles are considered to have a size such that the solid particles are predominantly sized less than 20 $\mu$m if greater than 75% of the total surface area of the particles is accounted for by particles having an average length of side of less than 20 $\mu$m.

In accordance with the invention it is more preferred that 95% of the total surface area is made of particles having less than 20 $\mu$m side length.

In a further preferred embodiment, the solid particles of ascorbic acid may have a size distribution such that the solid particles are predominantly sizes less than 15 micrometers. More preferably, the solid particles are predominantly sized less than 10 $\mu$m. In a preferred example the solid particles are predominantly sized less than 6 $\mu$m.

Examples of pharmaceutically acceptable carriers include those selected from the group consisting of polyhydric alcohols including alkylene glycols, (particularly propylene glycol) and glycerol; alcohols such as ethanol and isopropanol; polyalkylene glycols such as polyethylene glycol; other ointment bases such as petroleum jelly and lanolin; and mixtures thereof.

The preferred carriers are inert organic liquids, that is, they do not undergo any appreciable reaction with ascorbic acid.

It should be appreciated that the above list is not exclusive as the present invention also encompasses the use of pharmaceutically acceptable carriers other than those specifically mentioned. Glycerol, propylene glycol and polyethylene glycol are preferred and glycerol has been found to be particularly useful. Preferably the carrier is essentially water free containing less than about 0.5% by weight water.

Preferably ascorbic acid is present in a concentration of up to 45% by weight or indeed up to 60% by weight of the composition and a minimum concentration of 1% (more preferably 5%) is preferred. The composition may be comprised in the range of from 20 to 45% by weight ascorbic acid.

The compositions of the present invention has been found to provide relief from symptoms and pain associated with rheumatoid and osteo-arthritis, soft tissue injury, various skin conditions such as acne, urticaria, psoriasis and mollusca contagiosa as well as alleviation of the symptoms and pain of sinusitis, rhinitus and hayfever. Compositions of the present invention may also be used to reduce or remove melanin blemishes and are suitable to be used for cosmetic purposes such as a make-up base.

The present invention provides in a further aspect, a method for the treatment and/or prevention of a disorder in a human or animal which comprises administering a composition according to the invention.

Compositions of the present invention have been found to be particularly efficacious in delivering the ascorbic acid by transdermal migration following topical application, and this is the preferred route for administration of the compositions. The compositions may also be administered orally or by parenteral or subdermal deposition.

The present invention also includes methods for producing the composition described herein.

Accordingly, in yet a further aspect, the present invention includes a method for producing a composition, which composition comprises a pharmaceutically acceptable carrier and an ascorbic acid, which method comprises heating a mixture of the pharmaceutically acceptable carrier and the ascorbic acid to a temperature at which the ascorbic acid is substantially dissolved in the carrier, said mixture containing an amount of ascorbic acid in excess of the solubility limit of ascorbic acid in the carrier at ambient conditions, and cooling the mixture under conditions such that a supersaturated solution is formed and/or sufficient crystals of ascorbic acid that form on cooling are sufficiently fine to facilitate transdermal diffusion. Preferably the crystals are predominantly sized less than 20 μm in average length of side.

The method of the present invention may be carried out by heating the carrier to the desired temperature and then adding the ascorbic acid. Alternatively, a mixture of ascorbic acid and the carrier may be produced at room temperature and subsequently heated to dissolve substantially all of the ascorbic acid. Preferably, the mixture is stirred whilst it is being heated.

The mixture may be heated by conventional means or by microwave radiation, which microwave heating being preferred. Preferably the mixture is heated to a temperature in the range of from 100° to 170° C. and more preferably 110° to 130° C. Preferably the minimum temperature required to obtain complete dissolution of the particles is used as the heating of ascorbic acid to excessive temperatures can result in decomposition.

The cooling step of the present invention may be used to control the particle size of any crystals of ascorbic acid that form. The cooling step may involve rapidly cooling the heated mixture to ambient or below ambient temperature. This quick cooling (or "shock cooling") of the mixture results in the formation of small crystals of ascorbic acid. Large crystals do not grow because the rapid cooling and resultant increase in viscosity largely prevents diffusion of ascorbic acid in solution to the crystals that may have nucleated and thus inhibits crystal growth and development.

Quench cooling may be achieved by placing the mixture in an ice bath, dry ice or water cooled jacket.

An alternative cooling step involves allowing the mixture to cool slowly. This cooling method may require that the mixture be viscous. The high viscosity of the mixture will largely prevent diffusion or reduce the rate of diffusion of dissolved ascorbic acid to any crystals of ascorbic acid that may nucleate. The result is crystals of ascorbic acid that are predominantly sized less than 20 micrometers. The viscosity of the mixture may be increased by adding viscosity modifying agents to the mixture. The pharmaceutically acceptable carrier may constitute the viscosity modifying agent. Examples of suitable viscosity modifying agents include polyethylene glycol and ointments based thereon, petroleum jelly and paraffin wax.

With some carriers for example, glycerol, if the heated solution in which the ascorbic acid is dissolved is cooled slowly without disturbance, the resulting clear supersaturated solution may be maintained in this form during storage at ambient temperature and even at low temperature, for example 0°–4° C.

It should also be appreciated that ascorbic acid particles may also be prepared by other methods, such as by grinding. Thus, compositions according to the present invention may also be prepared by mixing a pharmaceutically acceptable carrier with organic active agent particles that are predominantly sized in accordance with desired diffusion characteristics. Typically they will be less than 20 micrometers.

The invention will now be described with reference to the following non-limiting examples.

EXAMPLE 1

A composition containing ascorbic acid was prepared by the method of the invention. 35.2 g ascorbic acid was dissolved in a heated solution containing 43.2 g propylene glycol and 5 g polyethylene glycol (20000) at 140° C. The solution was cooled to about 100° C. and then rapidly cooled in a jacketed vessel to 4° C. with stirring, until the material became a very viscous cream. It was bottled and a sample examined by optical microscopy.

For comparative purposes, unformulated crystals of commercially available ascorbic acid were examined. In the simple mixing of the crystals with a carrier, it is expected that the particle size of the crystals would not be markedly altered.

Both the comparative mixture and the composition produced according to the invention were examined under a microscope. The comparative mixture had ascorbic acid crystals that were approximately square shaped (equidimensional). The ascorbic acid crystals of the composition of the invention contained crystals of varied shape, with equidimensional crystals being the most common.

The particle size of the crystals were determined by microscopic examination. It was assumed that the crystals were of a constant thickness. The surface area of each crystal was then determined, and the particle size calculated by calculating the square root of the measured surface area. This value was then taken to be the length of side. The total area of the counted particles was measured and the sum of the areas of the different size ranges estimated as a percentage of the total. The results were:

TABLE 1

| Ascorbic Acid-Carrier Composition According to the Present Invention ||
|---|---|
| Size range. | Percentage Particles in Size range |
| <2 μm | 12.7 |
| 2–5 μm | 42.5 |
| 5–10 μm | 45.8 |

TABLE 2

| Unformulated Ascorbic Acid: Comparative Example ||
|---|---|
| Size range. | Percentage Particles in Size range |
| 10–20 μm | 0.36 |
| 20–50 μm | 0.57 |
| 50–100 μm | 2.7 |
| >100 μm | 96 |

As can be seen by comparing the data in Tables 1 and 2, the composition of the present invention has ascorbic acid particles with a much smaller particle size than that of the comparative example.

Tests using radioactive labelled ascorbic acid have shown that the ascorbic acid, when formulated according to the method of the present invention, is capable of migrating transdermally and becoming biologically available.

EXAMPLE 2

Two compositions comprising ascorbic acid and glycerol were produced. Composition A was produced by adding 3 parts ascorbic acid by weight to 7 parts glycerol by weight. The mixture was heated to 120°–130° C. to dissolve the ascorbic acid. The heated mixture was quenched by adding dry ice. Ascorbic acid particles present in composition A were predominantly in the size range of 2–10 microns.

Composition B was prepared by mixing $C^{14}$ labelled ascorbic acid with unlabelled ascorbic acid. The ascorbic acid was dissolved and recrystallised to ensure adequate mixing of the labelled and unlabelled ascorbic acid. The recrystallised ascorbic acid was broken up in a mortar and pestle and sieved through a nylon sieve. Particles in the range of 50–100 microns were collected and mixed with glycerol in a weight ratio of 3 to 7. No attempt was made to heat this mixture.

Composition A was applied to two laboratory rats and ascorbic acid levels in blood and urine were measured over a six hour period and the mean of the two rats determined at each time period.

The same tests were conducted on two other laboratory rats using composition B. The results were plotted to show the variation of ascorbic acid match and are shown in the attached drawings.

Figure 1:
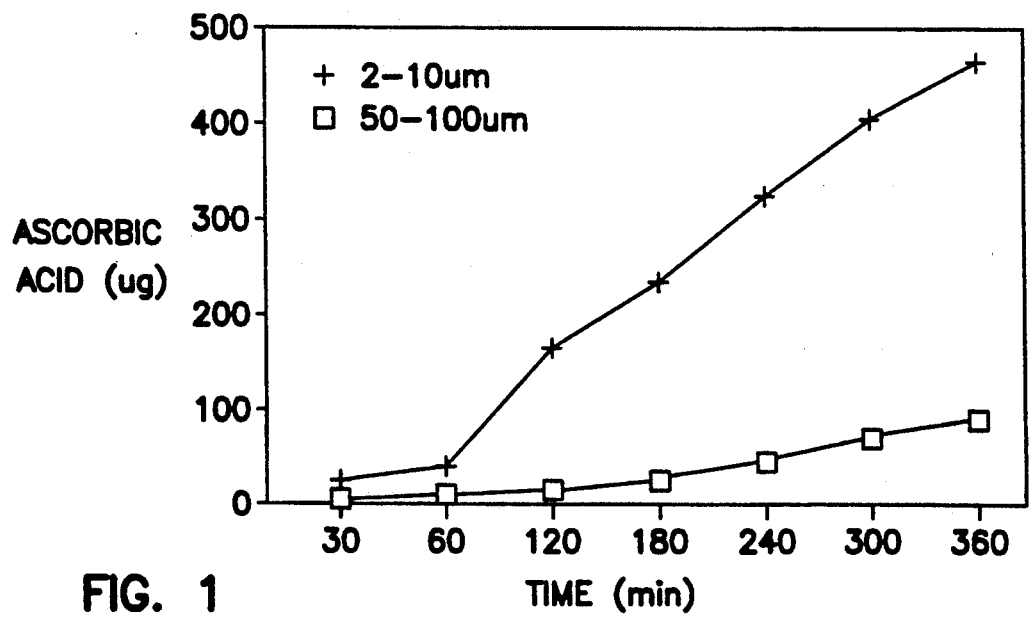
FIG. 1 is a graph showing the variation of ascorbic acid concentration in urine in the period of 6 hours of the topical application of composition A (size 2–10 microns) and composition B (50–100 microns).
Figure 2:
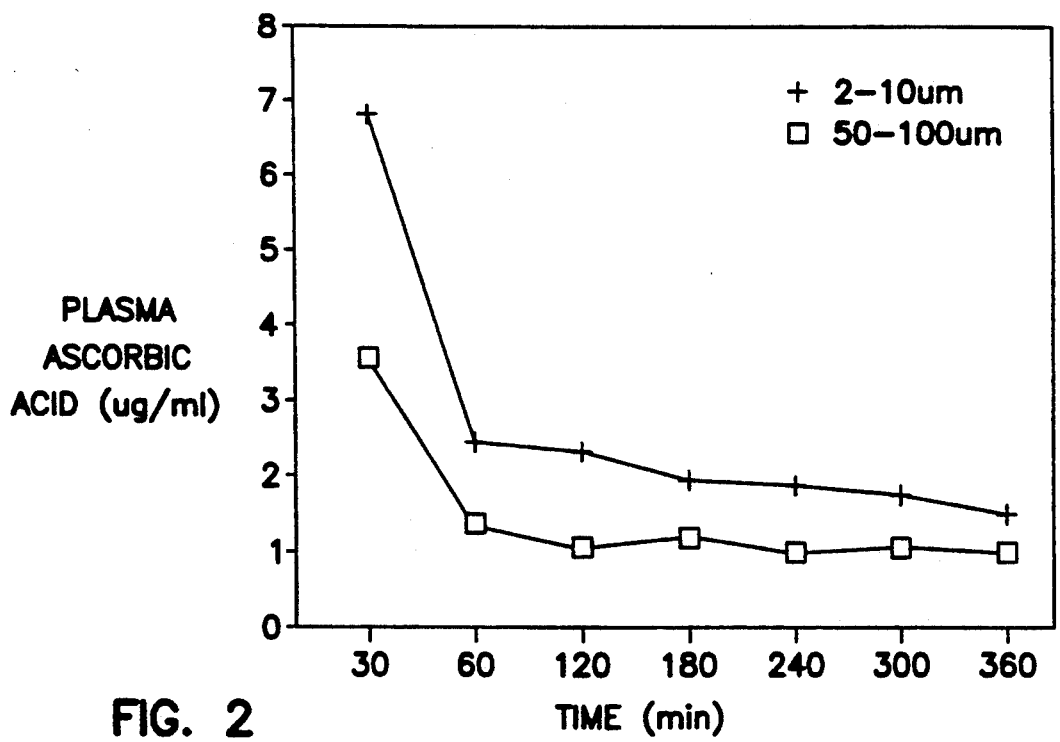
FIG. 2 is a graph showing the variation of blood plasma ascorbic acid concentration in the period of 5 hours of the topical application of composition A (size 2–10 microns) and composition B (50–100 microns).

We claim:

1. A composition for use in transdermal administration of ascorbic acid to a subject; said composition comprising:
   (a) a carrier of a composition effective for topical application of the composition to a subject, to achieve transdermal delivery of ascorbic acid; said carrier being selected from the group consisting essentially of: glycerol; propylene glycol; polypropylene glycol; polyethylene glycol; ethanol; isopropanol; petroleum jelly; lanolin and mixtures thereof; and,
   (b) 1 to 60% by weight of ascorbic acid in suspension within the carrier; the ascorbic acid in suspension comprising:
   (i) fine particles of ascorbic acid predominantly sized below 20 microns.

2. A composition as claimed in claim 1 wherein said ascorbic acid is present in the composition in an amount of up to 45% by weight.

3. A composition as claimed in claim 2 wherein said ascorbic acid is present in an amount of from 20–45% by weight of the composition.

4. A composition according to claim 1 wherein said composition further comprises one or more of a stabiliser, a dispersion agent, an emulsifier, and a thickening agent.

5. A composition according to claim 1 wherein said fine particles of ascorbic acid suspended within the liquid carrier comprise predominantly particles within a size range of 2–10 microns.

6. A composition according to claim 1 wherein particles comprises at least 95% of a total particulate surface area represented by the ascorbic acid in suspension comprise particles having a maximum side length of less than 20 $\mu$m.

7. A composition according to claim 1 wherein said carrier is selected from the group consisting essentially of: glycerol; propylene glycol; polypropylene glycol; polyethylene glycol; ethanol; isopropanol; and, mixtures thereof.

* * * * *